(12) United States Patent
Van de Velde

(10) Patent No.: US 9,789,002 B2
(45) Date of Patent: Oct. 17, 2017

(54) ELECTRONIC OPHTHALMOSCOPE FOR SELECTIVE RETINAL PHOTODISRUPTION OF THE PHOTORECEPTOR MOSAIC

(71) Applicant: Frans J. Van de Velde, Boston, MA (US)

(72) Inventor: Frans J. Van de Velde, Boston, MA (US)

(*) Notice: Subject to any disclaimer, the term of this patent is extended or adjusted under 35 U.S.C. 154(b) by 19 days.

(21) Appl. No.: 14/474,125

(22) Filed: Aug. 30, 2014

(65) Prior Publication Data

US 2014/0371731 A1    Dec. 18, 2014

Related U.S. Application Data

(63) Continuation of application No. 12/802,768, filed on Jun. 14, 2010, now Pat. No. 8,851,679.

(51) Int. Cl.
| | |
|---|---|
| *A61B 3/00* | (2006.01) |
| *A61F 9/008* | (2006.01) |
| *A61B 3/10* | (2006.01) |
| *G01B 9/02* | (2006.01) |

(52) U.S. Cl.
CPC ............ *A61F 9/008* (2013.01); *A61B 3/0008* (2013.01); *A61B 3/0075* (2013.01); *A61B 3/102* (2013.01); *A61B 3/1025* (2013.01); *G01B 9/0203* (2013.01); *G01B 9/02014* (2013.01); *G01B 9/02091* (2013.01)

(58) Field of Classification Search
CPC ....... A61B 3/1015; A61B 3/103; A61F 9/008; A61F 2009/00872; A61F 2009/00887
USPC ......... 351/200, 205, 206, 221, 246; 606/4–6
See application file for complete search history.

(56) References Cited

U.S. PATENT DOCUMENTS

| | | | |
|---|---|---|---|
| 6,186,628 B1* | 2/2001 | Van de Velde | 351/205 |
| 2008/0077121 A1* | 3/2008 | Rathjen | 606/5 |

* cited by examiner

*Primary Examiner* — James Greece

(57) ABSTRACT

An electronic SLO/OCT ophthalmoscope is equipped with a femtosecond (fs) laser for intra- or preretinal therapeutic use in the posterior segment of the eye. In one application the retina photoreceptor mosaic or Bruch's membrane is disrupted in such pattern that minimizes loss of visual functioning but reduces metabolic load of the outer retina. Using a beam splitter, one embodiment combines the SLO/OCT scanning beams with the therapeutic fs beam and an aiming beam. The therapeutic channel uses an independent x/y positioner and micro-deflector. Because the duty cycle is appropriate, a second embodiment can use the SLO/OCT scanners to also simultaneously scan a modulated therapeutic laser beam. A biometric OCT probe can be integrated in both configurations for focusing purpose. A method is disclosed to represent focus relevant tilting of the retina in the posterior pole. A derived apodizing "Stiles-Crawford" pupil weighting function is also independently useful for calculating light efficiency throughput of the anterior eye optics (cornea and iol/natural lens) in various circumstances.

8 Claims, 3 Drawing Sheets

ELECTRONIC OPHTHALMOSCOPE FOR SELECTIVE RETINAL PHOTODISRUPTION OF THE PHOTORECEPTOR MOSAIC

CROSS REFERENCE TO RELATED APPLICATIONS

Present application is a continuation continuing application of parent application Ser. No. 12/802,768, filed on Jun. 14, 2010. This application is also related to U.S. Pat. Nos. 6,789,900, 7,374,287 and 7,703,922.

BACKGROUND

Field of Invention

The invention relates generally to instruments for examining and treating the eye, and specifically to a version of the electronic ophthalmoscope combining SLO (scanning laser ophthalmoscopy) and OCT (optical coherence tomography) designs, and further equipped with an ultra fast pulsed laser source for administering selective retinal photodisruption laser therapy to the photoreceptor mosaic layer of the retina.

Description of Prior Art

The ophthalmoscope is well known as an important device for examining the eye, and in particular the retina. As a result of great interest in preserving eyesight, ophthalmoscopes of various constructions have been built. An electronic version of the ophthalmoscope, as described in U.S. Pat. Nos. 7,374,287 and 7,703,922, combining optimally scanning laser and optical coherence technologies, is particularly appealing because of its unique capability of combining a high resolution and high contrast 3-D infra-red or angiographic "real-time" video imaging of the retina with psychophysical procedures such as microperimetry (MP). A precise correlation between retinal anatomy and retinal functioning can be established with the scanning laser ophthalmoscope. This retinal function mapping reveals information about fixation behavior, visual acuity and retinal sensitivity, and is now known to be very helpful to the surgeon when applying various forms of therapeutic laser and for the purpose of low vision rehabilitation.

Van de Velde has disclosed before in U.S. Pat. Nos. 5,892,569, 5,923,399, 5,943,117, 6,186,628 and 6,789,900, which are all herein incorporated by reference, different embodiments of the relaxed confocal scanning laser ophthalmoscope that use various external light sources for therapeutic and diagnostic applications. Such functional extensions rely to a great extent on a relaxed confocal optical design of the SLO, incorporating one or two synchronized avalanche photodetector pathways that feed their signal into a versatile overlay frame grabber imaging board. U.S. Pat. No. 6,789,000 describes methods to selectively deliver therapeutic laser energy to the retinal pigment epithelium (RPE). They employ for example acousto-optic technology to create an appropriate duty-cycle for the laser applications. The short duration thermal applications are intended to limit the destructive laser tissue impact to the RPE layer. The delivery of sufficient energy to the photoreceptor layer (PR) in a confined manner and sparing as much as possible the choriocapillary layer (CC) and inner retinal layers, remains challenging. The aforementioned electronic ophthalmoscope can be equipped with newer short pulse femtosecond laser sources to achieve this goal.

Additional technical information regarding the electronic ophthalmoscope and its possibilities, especially with regard to the treatment of various forms of age-related maculopathy (ARM), can be found in the following texts, all included by reference:

1. Frans J. Van de Velde. Quantitative SLO microperimetry for clinical research in age related maculopathy. In: Noninvasive assessment of the visual system: from the Topical Meeting Vision Science and its Applications, Jan. 31-Feb. 3, 1997, Santa Fe, N. Mex./edited by Dean Yager; sponsored by Optical Society of America; in cooperation with the American Academy of Optometry. Published/Created: Washington, D.C.: The Society, 1997: 42-47. ISBN: 1557524718 (Library of Congress).
2. Frans J. Van de Velde. Role of the scanning laser ophthalmoscope in photodynamic therapy of macular disease Publication: Proc. SPIE Vol. 3908, p. 190-201, Ophthalmic Technologies X; Pascal O. Rol, Karen M. Joos, Fabrice Maims; Eds. Publication date: June 2000.
3. Frans J. Van de Velde. Scanning laser ophthalmoscope optimized for retinal microphotocoagulation. Publication: Proc. SPIE Vol. 3564, p. 146-157, Medical Applications of Lasers in Dermatology, Cardiology, Ophthalmology, and Dentistry II; Gregory B. Altshuler, Stefan Andersson-Engels, Reginald Birngruber, Peter Bjerring, Adolf F. Fercher, Herbert J. Geschwind, Raimund Hibst, Herbert Hoenigsmann, Frederic Laffitte, Henricus J. Sterenborg; Eds. Publication date: February 1999.
4. Frans J. Van de Velde et Al. Scanning laser retinoscopy: a new technique for evaluating optical properties of the cornea after refractive surgery Publication: Proc. SPIE Vol. 3192, p. 187-194, Medical Applications of Lasers in Dermatology, Ophthalmology, Dentistry, and Endoscopy; Gregory B. Altshuler, Reginald Birngruber, Marco Dal Fante, Raimund Hibst, Herbert Hoenigsmann, Neville Krasner, Frederic Laffitte; Eds. Publication date: December 1997.
5. Frans J. Van de Velde. Scanning laser ophthalmoscopy: optimized testing strategies for psychophysics Publication: Proc. SPIE Vol. 2930, p. 79-90, Lasers in Ophthalmology IV; Reginald Birngruber, Adolf F. Fercher, Philippe Sourdille; Eds. Publication date: December 1996.
6. Volume 302 Proceedings of the Bull Soc Belge Ophtal, 2006, all papers.
7. Frans J. Van de Velde. Electronic Ophthalmoscopy: Functional 4-D imaging of the retina. Thesis Universiteit Antwerpen, 2009, ISBN 978-90-5728-224-9.

OBJECT AND ADVANTAGES OF THE INVENTION

It is the principle object of this invention to disclose additional embodiments and optical configurations of the electronic ophthalmoscope. They incorporate the use of short-pulse lasers, specifically in the femtosecond domain, to selectively photodisrupt in a predetermined pattern the photoreceptor mosaic layer of the retina or Bruch's membrane.

An imaging or biometric OCT channel will be of help to focus the therapeutic beam onto the targeted layer, and also to assess morphologically the effect of the treatment.

MP will be of use to assess the need for treatment in particular areas of the retina, and also to evaluate the results of such treatment from a psychophysical perspective, with a high degree of spatial correspondence between the areas of treatment and subjective evaluation.

In summary, the improvements to the electronic ophthalmoscope for the purpose of selective laser treatment to the photoreceptor layer or Bruch's membrane include:

1) The incorporation of an appropriate novel therapeutic laser source, providing an optimized duty-cycle and 3-D spatially well-defined laser-tissue interaction.
2) An imaging channel, e.g. based on confocal detection and/or coherent detection, capable of viewing the retina in 3-D under optimal fiduciary conditions for such treatment modality.
3) An auxiliary OCT biometric channel or probe that will assist in positioning the therapeutic laser beam in depth along the z-axis.
4) Optimizing the optical quality of the eye for such treatment; including (a) the use of adaptive optics technology as described in the references, and (b) performing routine elective "Bag-in-the-lens" surgery for removing the natural lens.

Further objects and advantages of the proposed embodiments will become apparent from a consideration of the drawings and ensuing description of a preferred embodiment.

DESCRIPTION OF THE DRAWINGS

Sheet 1 of 3: Anatomical and Physiological Context

Sheet 2 of 3: Instrument Configurations

Figure 10:
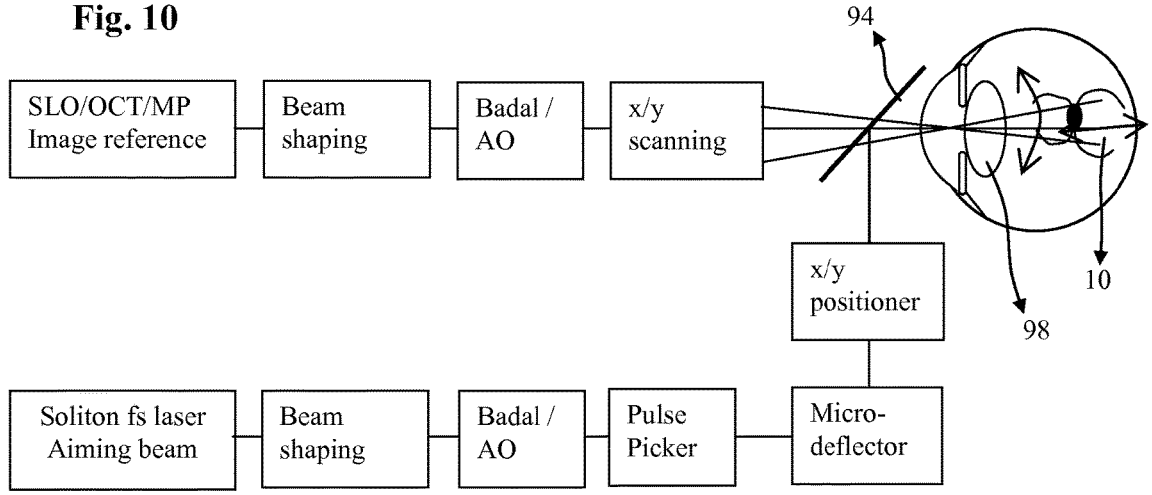

FIG. 10 illustrates a generic combination of an electronic ophthalmoscope as described in U.S. Pat. Nos. 7,374,287 and 7,703,922, with a fs therapeutic laser source, as in U.S. Pat. No. 6,789,900. The SLO and OCT beams as well as the aiming beam and fs laser can be of approximately 530, 800 or 1050 nm wavelength. Beam shaping typically involves truncation, collimation at various diameters, polarization control. Focusing typically involves control of spherical defocus, astigmatism, and optional beam shaping with a deformable mirror. The x/y scanners are for example a combination of galvo and polygon for the SLO/OCT/MP part and an x/y positioner as described in U.S. Pat. No. 6,789,900 for the fs laser. The pulse picker for the fs laser can be an AOM, the micro-deflector can be a two-dimensional AOD with appropriate collimators, or a double galvo-mirror assembly.

Figure 6:
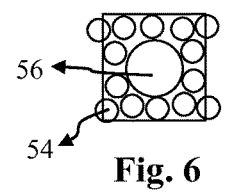
FIG. 6 represents a tangential section through the retina of 10 by 10 mu, at circa 6 to 7 deg of eccentricity between the optic disc margin and fovea, just proximal to the level of the OS/IS junction 30, 70, 74. A central cone 56 of diameter of 4.5 mu is surrounded by multiple rods 54 of about 1.5 mu diameter, with intercellular matrix in between. Towards the fovea the number of rods diminishes, being replaced by cones, and the cone diameter reduces to 2 mu; towards the periphery the number of cones reduces as they are replaced with rods. This sectional area corresponds approximately to a desired FWHM 10 mu focused spot of the therapeutic fs laser beam. It also corresponds to an individual subunit of treatment 58, 60 as in FIG. 7.
Figure 11:
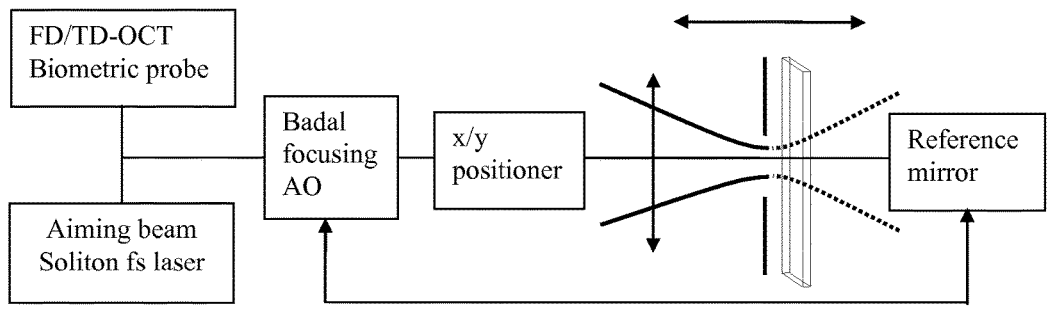

FIG. 11 An TD/FD OCT biometric channel or probe can have a common optical path with the fs laser beam or aiming beam, including multiplexed or common light sources. A x/y positioner or micro-deflector as in FIG. 10 can be used for biometric purposes or averaging the OCT signal over a small area as represented by FIG. 6. A link between the reference mirror position and Badal focusing unit can then provide a lock-in on specific layers of the retina, in particular the IS/OS junctional complex.

Figure 12:
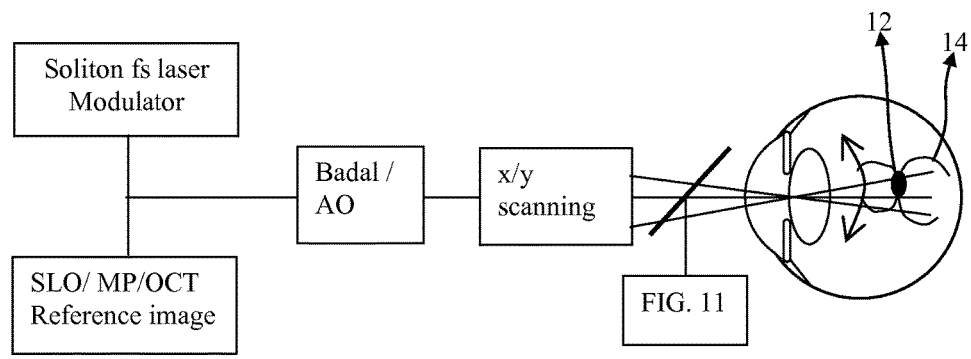

FIG. 12 The SLO/MP channel can have a common optical path with the fs laser, including multiplexed or common light sources. The same scanners as in FIG. 10 can be used for both imaging of the retina in an SLO confocal mode and precise targeting of a modulated fs laser beam, as would the beam for MP purpose. Different beam diameters can be combined. This configuration is possible because the duty cycle of the fs laser is appropriate. An OCT/aiming beam combination as in FIG. 11 for biometric and focusing purposes can be coupled to the SLO/fs laser with the help of a beam splitter and x/y positioner as in FIG. 10 (not shown).

Sheet 3 of 3: Directionality Index Determination

Figure 13:
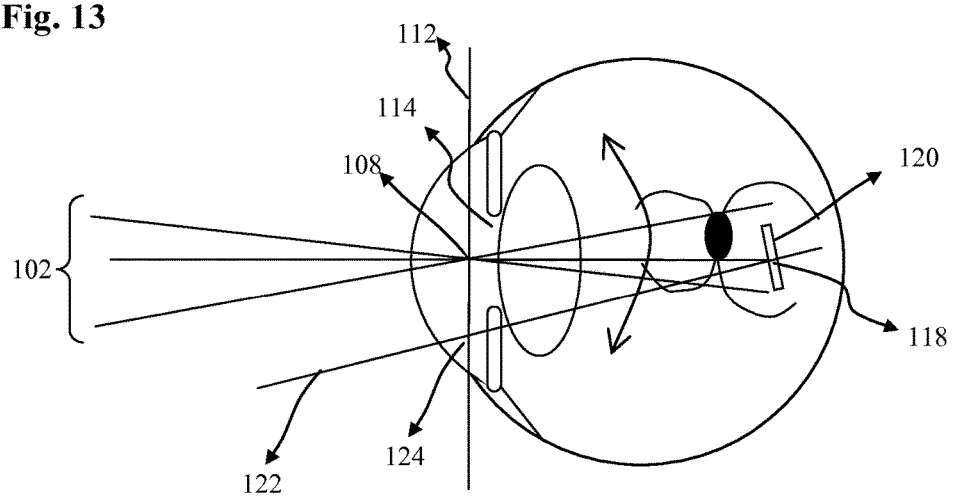

FIG. 13 illustrates the approximate position of the pivot point 108 of the OCT scanning system within the eye. It is optimally positioned in the middle of the exit, entrance 112 and anatomical pupil 114 of the eye. This is accomplished by centering fixation 16 in the middle of a fuzzy vignetting circle defined by the pupil margin 114 on the reference fundus image; the optimal depth location is determined as the middle position between start of proximal and distal vignetting of the image while moving the instrument along the z axis. There is some tolerance, especially if no significant ametropia is present. The inclination of a tangent plane 120 to the retina at the fixation location 16, 118 is indicated, as well as the normal 122 to this plane and the intersection 124 of this normal line with the approximate position of the pupillary plane 112.

Figure 14:
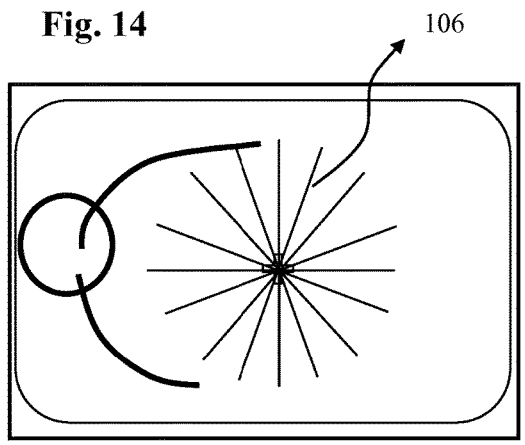

FIG. 14 lines 106 mark the position of a set of radial B scans 104 centered on the foveal fixation location 16, 118. Other patterns can be used centered on any location in the posterior pole 10 of the eye.

Figure 15:
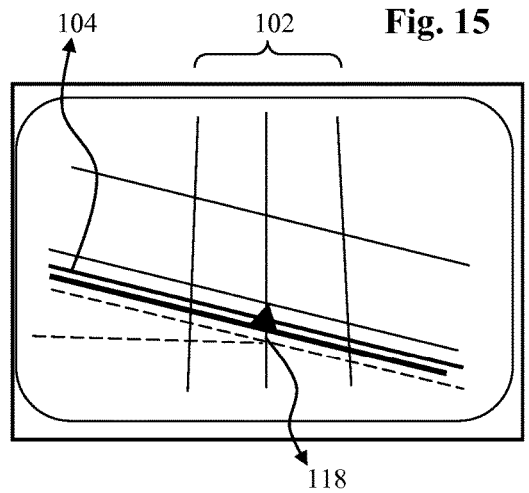

FIG. 15 shows the inclination angle of the slightly curved reference layers in a particular B scan 104 relative to a horizontal reference line, tangent to a chosen retinal location e.g. 16, 118. From the set of inclination angles corresponding to the set of radial B scans 104 of FIG. 14, the best fit inclination or tilting of a tangent plane 120 in space at the fixation and foveal location 16, 118 can be determined.

Figure 16:
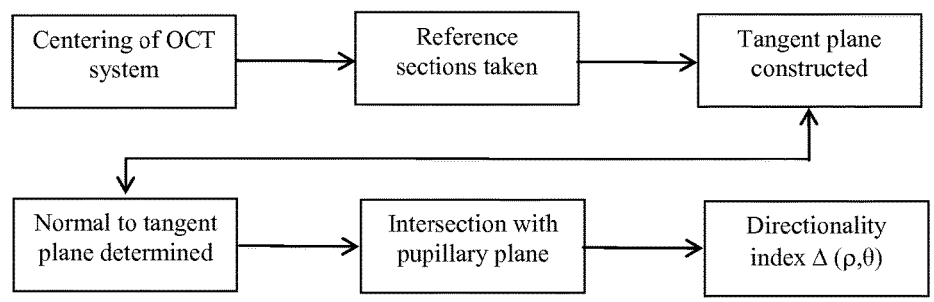

FIG. 16 is a flow chart illustrating the procedural steps necessary to derive a directionality index Delta (rho, theta) with rho corresponding to the distance of the intersection 124 to the center of the pupils 114 in mm or alternatively to the efficiency percentage of the Stiles-Crawford curve. Theta corresponds to the angular location of this intersection 124 relative to the pupil 114, in degrees. Ten percent of the general population is estimated to have a rho value exceeding 3 mm, possibly severely impairing night driving as loss of contrast sensitivity is expected when focal head lights constrict the anatomical pupil 114 of the eye, with multifocal iols, and in refractive surgery.

REFERENCE NUMERALS IN DRAWINGS

Figure 1:
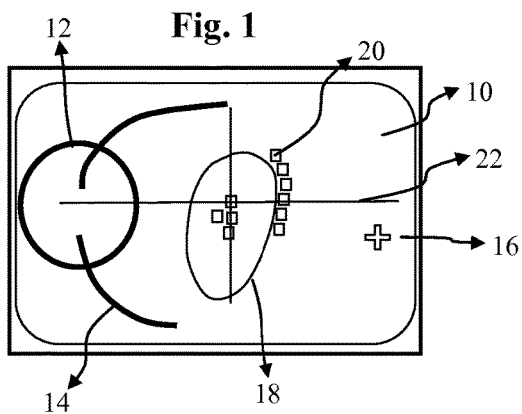
FIG. 1 is an overview of the retina 10, as seen at video-rate in real-time on a TV monitor (600 by 480 pixels). This image for example can be produced by the fiduciary infra-red 800 nm SLO channel. The field-of-view is about 20 deg diagonal, representing circa 1.5 to 1.75 minarc per pixel, equivalent to 8 mu/pixel. The optic disc 12, 1500 mu or 5 deg in diameter, and major blood vessels 14 are visualized. The subject focuses on a small fixation cross 16 presumably positioned at the foveal location. A retinal lesion 18 is delineated between the optic disc and fovea. Little squares 20 represent laser applications or psychophysical stimuli of about 100 mu on a side, corresponding to approximately 10-12 pixels or Goldmann III equivalent size. Vertical and horizontal lines 22 indicate the precise location of corresponding imaging OCT sections through the retina.
Figure 2:
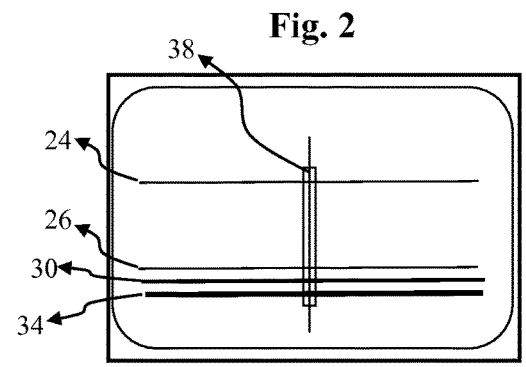
FIG. 2 details on a separate but concurrent video image the OCT section referenced in FIG. 1. This section indicates the highly reflective reference layers of the retina: (1) RPE layer 34, often represented as a double line representing (a) Bruch's membrane (BM) 86 and outer parts of the RPE cells with mitochondria and tight junctions, (b) the inner parts of the RPE cells with photoreceptor end-tips and melanin granules, (2) the junctional layer of the IS/OS parts of the photoreceptors 30, (3) a much less pronounced OLM layer 26 with tight junctions, (4) the ILM layer 24. The elongated rectangular image part represents the immediate neighborhood, e.g. 10 by 10 mu, of a treatment area or laser beam trajectory 38 as represented in FIGS. 3, 4 and 5.

10 posterior pole of the left eye, field of view (FOV) of approximately 20 deg diagonally (12×15 deg).
12 optic disc, reference 1500 mu or 5 deg diameter
14 large retinal blood vessels, typically 100 to 150 mu diameter
16 fixation cross
18 outline of lesion, either patch of chorioretinal atrophy or area of depressed absolute retinal sensitivity
20 outline of individual laser applications or psychophysical stimuli, about 100 mu on a side
22 vertical or horizontal section of OCT (as represented in FIG. 2)
24 inner limiting membrane, ILM
26 outer limiting membrane, OLM
30 junctional complex inner and outer segments of photoreceptors, IS/OS junction, key reference layer
34 retinal pigment epithelium layer, RPE, sometimes appears as double line
38 A-scan equivalent of laser beam trajectory through retina (SLO, OCT, MP or therapeutic beam)
42 inner retinal layers including ILM, NFL, GCL, IPL, INL, OPL
46 outer retinal layers including HFL, ONL, OLM, IS PR, IS/OS, OS, RPE, BM, CC
50 virtual location of reference mirror position (coherence gated OCT channel), high z-axis resolution
52 virtual location of confocal aperture (confocal gated SLO channel), low z-axis resolution
54 rod
56 cone
58 untreated subunit of application
60 treated subunit of application
62 Henle's fiber layer, HFL
64 outer nuclear layer, cone layer and multi rod layer, ONL
66 outer limiting membrane, microvilli of Müller cells, tight junction complex, OLM
70 inner proximal segments of cone and rods photoreceptors PR, mitochondria in distal part, IS
74 IS/OS connecting region with cilia, key reference layer on OCT, IS/OS
78 outer segments of cones and rods PR containing photopigment, OS
82 retinal pigment epithelium cells with inner proximal (end-tips PR) and outer distal part, RPE
86 Bruch's membrane composed of 5 distinct layers including middle elastin layer, BM
90 capillary network of the inner choroid layer, CC
94 beam combining element, post-scanners
98 natural lens or replacement intra-ocular lens, e.g. "Bag-in-the-lens" intra-ocular lens
102 bundle of A scans OCT including central fixation scan 104 single B scan created by array of A scans, showing slightly curved retinal layers
106 star figure indicating radial set of B scans centered on fixation
108 pivot point of scanning OCT beam
112 plane of optical entrance and exit pupil of the eye (very close to each other)
114 anatomical pupil of the eye (often interchanged with 112 in applications)
118 central fixation, corresponding foveal location
120 tangent plane to the global set of B scans at fixation 106, also extended retinal area
122 normal to the tangent plane 120 at fixation 118
124 intersection of normal 122 with plane 112
List of Other Abbreviations and Symbols Used
SLO scanning laser ophthalmoscope, ophthalmoscopy
OCT optical coherence tomography
MP microperimetry
ARM age related maculopathy
FOV field of view
^, *, / denote respectively "to the power of", "multiplied by", "divided by"
$\theta, \mu, \lambda, \rho, \Delta, \pi$ respectively denote theta, mu, lambda, rho, Delta, pi
z(½) depth location, defined at particular location between parentheses, typically at half depth
w(f) waist radius at particular location indicated between parentheses, e.g. at focus or original
a( ) absorption or attenuation coefficient for particular wavelength and absorber
d diameter
deg degree(s)

DETAILED DESCRIPTION AND OPERATION OF THE INSTRUMENT

Representative embodiments of the electronic ophthalmoscope have been described in U.S. Pat. Nos. 7,374,287 and 7,703,922. The art of combining such instrument with various therapeutic light sources of different pulse duration has been described in U.S. Pat. Nos. 5,892,569, 5,923,399, 5,943,117, 6,186,628 and 6,789,900.

The principles and applications of scanning laser ophthalmoscopy, optical coherence tomography and microperimetry are also described in detail in the publications referenced before. Below we describe the operational environment of an ophthalmoscope that is capable of selectively disrupting in a controlled manner a pre-defined part of the photoreceptor mosaic of the retina or Bruch's membrane.

I. Anatomical and Physiological Considerations

Figure 9:
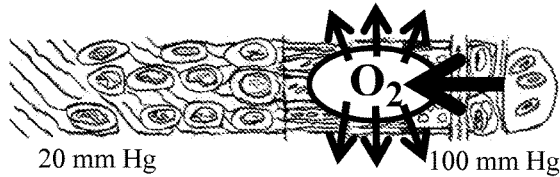
FIG. 9 is similar to FIG. 8. Representation of what happens to the oxygen gradient in the outer retina when a patch of photoreceptors 70, 78 and possibly also RPE cell(s) 82 are disrupted. An "oxygen fountain or window" is created as predicted in the references. Physiologically, a saturated capillary O2 tension of about 100 mm Hg (100%) diminishes gradually across the RPE-photoreceptor complex as indicated. This tension reaches a basal value of about 20 mm Hg just proximal to the ONL 64 and remains circa at that level throughout the inner retina because of the oxygen supply of the inner retinal circulation. The oxygen not consumed after successful photodisruption will diffuse into the adjacent retina. Perforations in BM 86 can have a similar effect.

The photoreceptor-RPE complex is by far the most active metabolic tissue in the human body, and even more so in the macular area. A huge volume of oxygen is needed to drive the Wald's visual cycle and to maintain the so-called dark current loop. In order to maintain an adequate oxygen gradient across this complex as indicated in FIG. 9, the choriocapillary circulation 90 possesses specific anatomical and physiological characteristics that are well known and not elaborated upon. A reduction in the very high choroidal blood flow, decreased arterial oxygen saturation level and likely far more important a decreased capability of diffusion of oxygen and metabolites across a thickened or altered Bruch's membrane 86 with elastic layer calcifications and densification, even amounting to a 10 to 15% chronic deficit, will result in a less than optimal starting oxygen tension at the basal side of the RPE cells 82 or a steeper oxygen gradient. This can in turn initiate a cascade of biochemical events leading to either apoptosis and chorioretinal atrophy or, often in younger individuals, to anatomically disruptive neovascularization. Both of these entities are well-known as the hallmarks of age related maculopathy (ARM), the leading cause of legal blindness in the United States.

Figure 7:
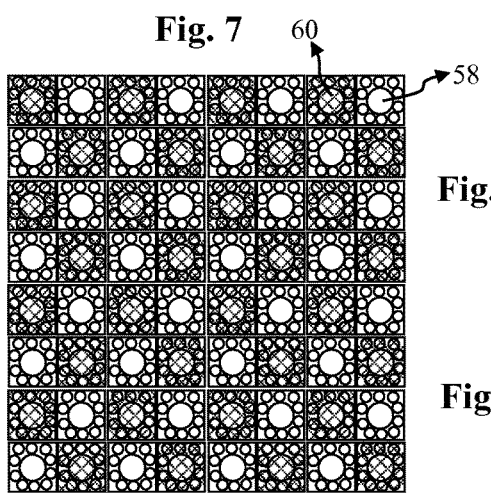
FIG. 7 illustrates the composite structure of a 100 by 100 mu laser application spot 20 mentioned in FIG. 1. It is composed of 10 by 10 subunits as in FIG. 6, treated 60 or untreated 58. A microdeflector is capable of treating the subunits in a specific on-off pattern within this application 20. Thus, in this particular one application about half of the cone receptors (and half of the rod population) will be disabled. Other configurations are possible.
Figure 8:
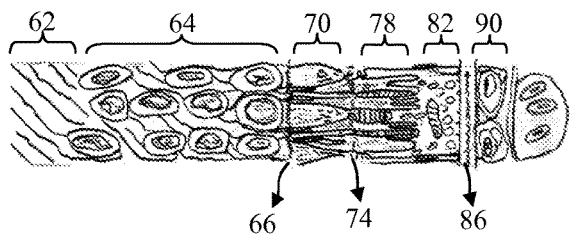
FIG. 8 illustrates a vertical histologic detailed section of the retina corresponding to FIG. 6. Indicated are (1) the choroid capillary layer CC (10 mu by 25 mu) 90, (2) Bruch's membrane BM (5 mu) 86 consisting of the basement membranes of endothelium cells and RPE cells, two collagen layers and an intermediate elastin layer, (3) The RPE cells (10-15 mu by 15-20 mu) 82 with an outer part having infoldings, nucleus and abundant mitochondria, an inner or proximal part 78 having melanin granules and villi surrounding the end-tips of photoreceptors, (4) the outer segments OS of photoreceptors 78 containing the photopigment (25-40 mu), long and cylindrical in the case of rods, shorter and conical in the case of cones, (5) a connecting region 74, containing a cilium to (6) the inner segments of rods and cones 70 that contain in their distal parts an abundance of mitochondria (25-40 mu), (7) a tight junction complex, OLM, 66 between the photoreceptors IS, and microvilli of Müller cells, (8) a (mono) layer of nuclei of the cones positioned adjacent to the OLM 66, and multiple additional layers of nuclei of rods 64, (9) the axons of the photoreceptors that bend characteristically in the macular area and constitute Henle's fiber layer 62.

We have proposed before to selectively deactivate in a well-defined pattern the metabolically very active photoreceptor population in the macular area. In particular the mitochondria rich ellipsoid part of the PR IS layer 70, at the IS/OS junction reference layer 74 is targeted, but optionally also the RPE layer 82. This "pruning" should be done in such manner that from a psychophysical point of view only acceptable changes to the subject's visual perception occur, while creating so-called "oxygen windows" or "fountains" that let unconsumed oxygen diffuse efficiently into the adjacent retina. A first precautionary principle here is sparing of the inner retinal layers 42, the ONL 64 and HFL 62, and avoiding damage to the choroid. A second principle is to confine the treatment in a targeted area to the smallest group of photoreceptors possible. FIG. 6 illustrates such a group, called subunit, consisting of a centrally located cone 56 surrounded by a circle of rods 54, at about 7 deg of retinal eccentricity. In between the treated subunits of an application 20 of e.g. Goldmann III size, as in FIG. 7, at least one cone and several rods are expected to be untouched 58. Even when taking into account the topographical changes that are described in the figure legends, a sufficient functional cone and rod density will be available to provide adequate retinal resolving power and sensitivity. The treatment might be limited to several densely spaced applications to the edges of existing patches of chorioretinal atrophy or it might be a ring of applications between 4 and 8 degrees of eccentricity. This treatment modality might also be of interest to reduce the metabolic load in the macular area of dystrophic disease entities such as Stargardt's. Intended or non-intended involvement of the ONL 64, RPE 82, BM 86 and CC layer 90 in the treatment application is discussed below. Perforating BM 86 by itself is of particular interest and may be all that is needed from a therapeutic point of view.

II. Available Therapeutic Laser Sources and their Mode of Action

At least for the wet form of ARM several distinct therapeutic approaches that all involve laser light of circa 800 nm wavelength but of dramatically different exposure durations have been developed. They are in part the object of invention in the referenced patents and referenced publications. Relatively long and extended exposure to light (in the order of $10^2$ of seconds) is used in photodynamic therapy (PDT), a technique based on a photochemical mode of action. The historically earliest form of laser treatment uses a thermal mode of action and relatively confined applications about $10^{(-1)}$ seconds. In order to selectively coagulate or vaporize the RPE cells and prevent the thermal damage from spreading beyond those cells, even shorter pulses in the microsecond range are applied. Thermal applications require a relatively strong absorber of light, in this case the abundant melanin granules of the RPE, to be present exclusively in the targeted volume. Thus, such methods cannot be used for selectively disabling the photoreceptors or drilling holes in Bruch's membrane. A suggestion was made in the related U.S. Pat. No. 6,789,900 to use a CW 1064 nm laser to exactly do this. However, a still relatively low absorption of light of this wavelength by water (melanin absorbs this wavelength far more efficiently) and the ubiquity of this absorber in and around the photoreceptors makes this approach rather problematic.

Shorter exposure duration lasers in the nanosecond, picosecond and femtosecond range, relying on a photodisruptive instead of thermal absorptive mode of action, have been introduced for surgical applications involving the cornea and lens of the eye. The recently introduced femtosecond laser has certain advantages over the nanosecond and picosecond range lasers that make them far more suitable for precision applications at the retinal level, our intended usage. A detailed theoretical explanation for these advantages is to be found in Ching-Hua Fan, applied optics vol. 40, nr. 18, pp. 3124-3131, 2001. In brief, they include the negligible heat diffusion, minimal plasma absorption and shielding effects, smaller laser fluences resulting in a high spatial resolution of the shape of the lesion, a deterministic optical breakdown rather than statistical permitting control of the ultra fast breakdown by changing the irradiated laser intensity. Also, the length of the pulse is shorter than or about the length of the focal volume, i.e. in the neighborhood of 30 mu for a 100 fs pulse. Within an approximate cylindrical volume of focus, the breakdown will start somewhere up the beam path and progress predictably toward the focus.

A good example of an appropriate femtosecond laser source is the "Origami—10" from OneFive GmbH, Switzerland. It has a tunable center wavelength between 1025 and 1070 nm, a pulse duration of 100 fs or less, a pulse repetition rate of 40 MHz (25 ns intervals) to 1.3 GHz (1 ns intervals), a peak pulse energy of 5 nJ (peak power of 22 kW), optionally higher. The output beam quality is diffraction limited. The pulses can be synchronized to an external clock. The bandwidth is transform limited according to $\tau(p)*\Delta(freq)=0.32$ resulting in a 30 nm Gaussian bandwidth. Similar sources of interest have a center wavelength between 514 and 532 nm and between 765 and 785 nm.

III. General Description and Control of the Optical Environment

We now consider in some more detail the impact of differences in absorption in vivo at 532, 800 and 1050 nm for water, melanin (melanosomes) and (oxy)hemoglobins. The law of Lambert-Beer, $I(x)/I(o)=e^{[-a*x]}$, can be applied. Also, Jacques has estimated the absorption coefficients a for RPE melanin in vivo for a range of wavelengths to be $a=[6.49*10^{12}*lambda(nm)^{(-3.48)}]$ [cm$^{-1}$] (Photochem. Photobiol. vol. 53, pp. 769-775, 1991). This results in values of 600/cm at 800 nm and 200/cm at 1050 nm. For reference at 532 nm the value is 1800/cm. From this we can conclude that as the wavelength increases, melanin gradually absorbs less, though still significant at 1050 nm. If we consider a layer of melanin pigment of 5 to 10 mu at the level of the RPE 82, then 10 to 20% of the intensity will be absorbed. In contrast, water absorbs insignificantly at 532 nm, minimally at 800 nm with an absorption coefficient of $2*10^{(-2)}$/cm, then steadily increases towards 1050 nm with an absorption coefficient of about $5*10^{1}$/cm, being a 40 fold increase. Yet, this is still insignificant at the PR/RPE level, but it of course explains why the initial intensity of a 1050 nm beam at the cornea is reduced to about 28% of its initial value at the PR layer (including both absorption and scatter effects). For oxyhemoglobin, predominantly present in the RBCs of the CC layer 90, absorption is very significant, but still less than for melanin, at 532 nm. It has some absorption in the 800 to 1050 nm wavelength interval, stronger than water. Some possibilities are predicted from the above data. The RPE 82 will be a relatively low resistance barrier to the photodisruptive effect of a focused fs laser beam, especially at 1050 nm. With sufficient intensity, single or repeat photodisruptive impacts can cross the RPE barrier 82 and further drill a hole into Bruch's membrane 86 and the inner very thin lining of the choriocapillary layer 90 endothelium cells. In itself, this could be of therapeutic benefit provided at least that the endothelium cells are capable of self-sealing. If the perforations are smaller than 8 mu, no RBCs can pass. With this in mind, a particular treatment protocol might use a more elaborate double laser beam exposure technique, the first application directed at removing the melanin barrier by destroying selectively RPE cells 82 in a manner described in previous patents. Another possibility is bringing a dye similar to fluorescein or indocyanin green into the retinal circulation at the time of treatment. This dye should absorb significantly around the center wavelength of the fs laser and will then act to protect the choriocapillary layer 90.

With aging, the natural lens of the human eye 98 can gradually develop a cataract, limiting considerably the possibility of diffraction limited imaging and therapy at the retinal level. Even before a manifest cataract develops, changes in the lens will include an increase in higher order aberrations and scattering of light. Such scattering will reduce transparency and again increase the size of the theoretical diffraction limited spot size. In order to avoid these problems and also to correct the eye's refraction as much as possible before fs laser treatment, an elective cataract surgery procedure can be performed using the "Bag-in-the-lens" intra-ocular lens of Tassignon, U.S. Pat. No. 6,027,531. In summary, this routine implantation technique allows a reliable active optical centration of the 5 mm optical diameter lens and prevents any secondary capsular opacification to occur. After stabilization, any remaining spherical or astigmatic error is corrected (this correction can be provided by the electronic ophthalmoscope or contact lens). It is useful to obtain with an aberrometer the Zernike polynomial coefficients of residual wavefront aberrations for an apodized 5 mm pupil and centered on the line of sight. It is also useful to obtain biometric data that are based on a reflective low optical coherence technique, such as optical path lengths. These data are now routinely collected pre and post cataract surgery.

We now introduce a practical index that will be of use in focusing the therapeutic laser beam over an extended area of the reference image 120 (much larger than an isolated application area 20) (FIG. 13, 14, 15, 16). Biometric parameters as discussed before relate to the foveal location 16, 118 and the line of sight for alignment. They do not adequately describe the general orientation of an extended retinal area 120 around fixation 16 or the intended application location 20. The normal line 122 to this retinal area 120 should optimally intersect the center of the exit pupil 112 of the eye. In that case, light will enter on average optimally along the optical axis of the cone outer segments and no Stiles-Crawford effect will be present. We propose calculating and representing the intersection 124 using routine OCT anatomical data taken from 12 clock hour sections 106 through the fovea 118, using the line of sight fixation procedure and fitting the minimally curved prominent reflective layers of the retina 104 to a tangent plane 120. This new biometric parameter will inform us how much "excess curvature of field" aberration to expect when focusing the therapeutic beam across a larger area on the retina. A better entrance location 108 for the therapeutic laser beam may then be available. This directionality index would also be useful in interpreting the well-known but difficult to measure Stiles-Crawford effect linked to the cone photoreceptor orientation in the perifoveal area.

IV. The SLO, OCT and Therapeutic Beams and Channels Beam Optics

We will first discuss generalities concerning the focusing of the different laser or superluminescent diode beams in our application, then proceed to a description of two preferred channel configurations.

Figure 3:
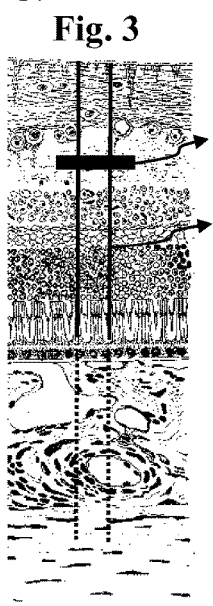
FIG. 3 illustrates a generic section through the retina, approximately halfway the fovea and optic disc margin at about 6 deg of eccentricity, approximately 350 mu or 1 D equivalent thickness. Indicated are the choriocapillary layer (CC), Bruch's membrane (BM), outer retinal layers 46, Henle's fiber layer and other inner retinal layers 42 including the inner limiting membrane (ILM). A light beam trajectory 38 used for OCT purpose is drawn. A coherence gated depth of focus, here approximately 10 mu, is illustrated by the location of the thick reference line 50. This location is itself determined by the position of the reference mirror in the OCT set-up.
Figure 4:
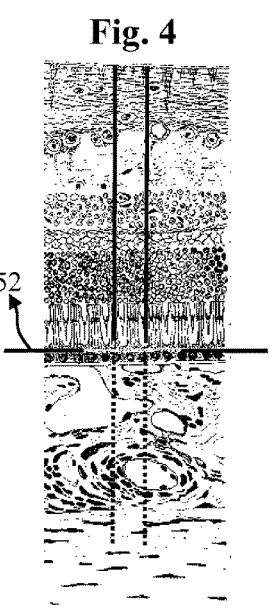
FIG. 4 is similar to FIG. 3 but with the representation of a confocal gated (SLO) depth of focus. The virtual location of a relaxed confocal aperture 52 of about 100 mu diameter is indicated at the waist level of a focused laser beam of 800 to 1000 nm wavelength. A Gaussian beam diameter of about 20 to 30 mu at waist level and 1 mm at the cornea will result in a Rayleigh zone or half-depth of focus of 600 mu.
Figure 5:
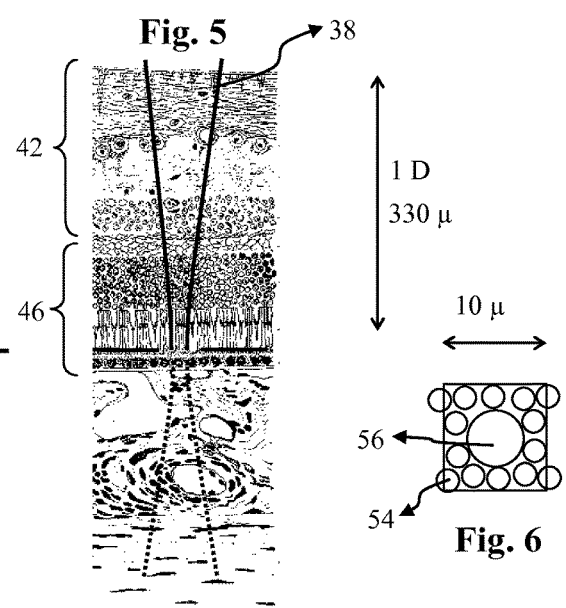
FIG. 5 is similar to FIG. 3 but with a laser beam of double entrance diameter, 2.2 mm or f/10, resulting in a twice smaller Gaussian spot size of 10 to 15 mu, and Rayleigh zone or half-depth of focus of 150 mu, four times smaller.

As a reminder, for Gaussian beams 38 (FIG. 3, 4, 5) that are used in a confocal gated configuration as the SLO, the following two relations are useful:

(a) The focused beam waist radius w(f)=lambda/pi*f(i)/w(o); for example a 2.28 mm diameter 1 mu beam (f/10) at the cornea is focused into a 12.5 mu Gaussian spot.

(b) The half-depth of focus or Rayleigh range z(½)=lambda/pi*[f(i)/w(o)]^2, in the above example the half-depth would therefore amount to 125 mu. Still a relatively large value. Of note is that the peak intensity of the laser beam is to be found on axis (rho=0) and for z=0. At z(½) this on-axis peak is reduced by half. As mentioned before, the focal volume length is larger than or equal to the actual femtosecond pulse length.

In contrast, for a broad-band light beam, laser or SLD, that is used in a coherence gated configuration 50 as in the OCT, the much smaller z-resolution is under certain conditions estimated as follows: 0.44 lambda(mean)^2/Delta (lambda); for a center wavelength of 1050 nm and bandwidth of 80 nm this would correspond to a z-resolution of 6 mu, at 860 nm this improves to 4 mu.

In practice our SLO, OCT and therapeutic beams are only approximately Gaussian. We have to take into account truncation effects and the beam quality or propagation factor M. In brief, the divergence angle theta=M^2 lambda/(pi*w (r)). This M^2 is better than 1.1 for the femtosecond lasers that we described.

We like to refer to a rule of thumb for estimating the practical focused FWHM diameter of beams. Both from an imaging and therapeutic perspective the FWHM diameter, instead of the 1/e^2 defined one, seems reasonable to use. Truncation, in the interest of saving power, will be limited to the unit ratio.

This rule of thumb is that the diameter at the focused waist is d=K*λ*f/#; where f(i) is the image focal length of 22.28 mm and K(FWHM)=1.13 if the truncation index is unity, i.e. the limiting aperture in the optical system is equal to the Gaussian diameter of the beam. More details can be found in the documentation from optical components manufacturer Melles-Griot.

From the foregoing it is evident that a near-Gaussian laser beam used at f/10 (with a FOV in the SLO of 20 deg diagonally, 1 pixel representing 1.6 minarc or 8 mu), at 500, 800 or 1000 nm will have a practical FWHM diameter at the focusing waist of 5, 8 and 10 mu respectively. It is important to note that this is sufficient for our diagnostic and therapeutic applications. In the case f/5 is used, those diameters are respectively halved, at least in theory, and some adaptive optics (spherical aberration) may be required.

In our embodiments a combination of 500, 800 mu and 1000 mu light sources are sometimes used. Therefore, differences in refraction index in a watery solution should be considered. Under fixed conditions of salinity, temperature etc, this refraction index is 1.3360, 1.3275 and 1.3250 respectively. A 0.75 D and 0.25 D difference in focusing between 550 nm, 800 nm and 1 mu can be adjusted for optically.

Channel Configurations

When considering options for coupling therapeutic laser sources to the scanning laser ophthalmoscope or another reference image device, an appropriate duty cycle for the therapeutic laser beam is of paramount importance, as is focusing. This has been explained in the referenced U.S. Pat. No. 5,892,569. For example, in a thermal photocoagulation procedure it is impossible to use the same scanning laser source for both imaging and therapeutic purposes as the scanning beam is only for less than 90 ns on a specific location, only to return 30 ms later to the same spot. Tissue temperature cannot be raised significantly in this way. The solution proposed in U.S. Pat. No. 5,892,569 is to couple and synchronize an external therapeutic beam with an x/y positioner to deliver pulses in the ms range.

Even when dealing with shorter duration pulses of 5 microseconds delivered at 2 ms intervals, in the microsecond regime for selective microphotocoagulation of the RPE, the SLO raster scanning is too fast. The solution here is to couple again an external therapeutic source to the SLO and to pass the beam through a second scanning system, e.g. an acousto-optic x/y microdeflector, to provide the correct duty cycle. In this manner the temperature can be raised in successive steps locally, even to the level of vaporization, without spreading significant heat to the neighboring tissue. The method has been reported in the referenced U.S. Pat. No. 6,789,900.

When using the femtosecond laser source to obtain photodisruptive effects in a watery solution, even shorter pulses in the order of 100 fs are applied at 25 ns to 1 ns intervals. This opens the possibility to use effectively the same scanning system or even scanning lasers for imaging and therapy, which is innovative. The method of using a second scanning system is also still possible. Each approach has some distinct advantages.

In FIG. 10 a generic SLO/OCT/MP electronic ophthalmoscope, as described in referenced U.S. Pat. No. 7,374,287, provides the fiduciary reference image of the fundus. This image can be a 40 deg diagonal FOV, 20 deg diagonal FOV, or even a 10 deg FOV, the latter possibly requiring adaptive optics implementation such as the use of a deformable mirror and wavefront sensing device. Fast x/y scanning is provided. Either 500, 800 or 1000 nm light sources can be used for the SLO/OCT/MP components. A beam splitter, switchable, is used to couple the imaging/microperimetry channel with the therapeutic channel. The latter comprises a femtosecond laser source described before and aiming beam configuration (possibly combined with a biometric OCT channel as later described). A separate micro-deflector and x/y positioner as in referenced U.S. Pat. No. 6,789,900 is used. The micro-deflector can be a double galvo combination or AOD. Initial focusing is done by using the biometric data as previously obtained, and a careful observation of the fundus appearance. In the absence of astigmatism and in the presence of clear eye media it is possible to see in the 20 deg FOV two major backscatterings of light while changing the amount of focus with the Badal mechanism: (1) the specular reflections of the ILM-nerve fiber layer and especially (2) the backscatter from the RPE layer, including reflections from a single or composite aiming beam. Several parallel pencils of light can be observed to merge into one image spot at the RPE level according to the well-known Scheiner principle. OCT biometric data will fine tune this focusing in a second stage (illustrated in FIG. 11). Morphologic feedback after trial exposures also aid in the optimal positioning of the beam waist. The advantage of the described optical set-up is the availability of a large FOV reference image.

In theory, when using a 10 deg FOV reference image, the laser beams operating at around f/5 will have a Rayleigh range of 30 mu and match therefore the length of the fs pulse. In the 20 deg FOV this would be around 125 mu as previously mentioned. Even if different layers are intentionally or not exposed between the RPE layer and outer part of the ONL, the expected therapeutic outcome might be similar. Thus, some uncertainty in focusing is tolerable.

In FIG. 11 is shown a composite aiming beam, of variable wavelength, and composed of a single pencil or multiple pencils of light, one of which can also be a fs laser beam or biometric OCT beam. This composite beam is targeted on the retina with an x/y positioner. Relative biometric data, i.e. the optical distances between a reference layer and the target layer are measurable even in the presence of eye movements along the z-axis. The reference reflection layer can be the anterior corneal surface. This data, combined with the biometric information obtained at the fixation location with other means, allows the calculation of the necessary Badal correction to position the beam waist as precise as possible at a given eccentric retinal location and depth.

In FIG. 12 the individual fs laser pulses are synchronized to the master clock of the fiduciary imaging system and modulated with the help of the imaging board. E.g. every pixel of 90 ns width can be precisely synchronized with the delivery of a single fs laser pulse or up to 90 fs laser pulses. Pulse interval can be as minimal as 1 ns. It is the task of the pulse picker to suppress unwanted pulse deliveries, to modulate the intensity of individual pulses and to maintain the appropriate duty-cycle.

An aiming beam configuration as in FIG. 11 is coupled to the optical set-up of FIG. 12 with the help of a switchable beam splitter and x/y positioner. This configuration can also include a biometric OCT channel as explained. Both 800 nm or 1000 nm wavelengths can be used.

V. Feedback

The therapeutic efficacy of the fs laser treatment modalities as described can be assessed both by subjective and objective means. The subjective method employs the non-invasive technique of microperimetry MP. This method has been extensively elaborated upon by the author in the references. In brief, absolute dark adapted thresholds and speed of recovery from bleaching are related to the amount of photopigment that is capable of catching light quanta and the rate of renewal of such photopigment. For example, cone functioning at 532 or 650 nm can be evaluated if the directionality of testing (entrance location) and pre-adaptation bleach are properly controlled. The application size equivalent to Goldmann III or a larger area can be used. Because of the specific neuronal processing of the signals coming from activated cones, an improvement could be detected after treatment. Other assessment strategies involving both cones and rods can be envisioned.

A very important role of MP is to verify that treatment will not adversely affect minimal retinal resolution and sensitivity levels in the treated areas. Another role as mentioned before is the possibility to predict the very early phases of ARM when such treatment can still postpone the onset of the disease by a decade or more.

The objective method of treatment assessment involves the measurement of actual PO2 values within the retina (Shonat et al., Applied Optics, vol. 31, nr. 19, pp. 3711-3718, 1992). This is an in-vivo invasive technique based on the principle phosphorescence lifetime imaging. The oblique incidence of a narrow 532 nm laser beam through the relevant layers can be used for this purpose. A porphyrin based dye is allowed to diffuse into the retina (intravitreal injection required). A Stern-Volmer relationship is used to convert lifetime phosphorescence to oxygen tension.

SUMMARY

Embodiments of an electronic ophthalmoscope capable of selectively photodisrupting the photoreceptor layer or perforating Bruch's membrane in a specific pattern have been disclosed. The operational environment necessary to realize this goal includes the following:

(1) Physiological considerations and rationale for treatment;
(2) Anatomical considerations including dimensional aspects;
(3) Desired short pulse laser sources and their physical properties of interest;
(4) Significant parameters of and control of the optical environment (intra-ocular scattering, absorption, tilting of retina);
(5) Beam optics, focusing issues;
(6) Preferred channel combinations;
(7) Ways to get feedback on the efficiency of the treatment.

Although the descriptions of preferred embodiments contain many specifications, these should not be construed as limiting the scope of the invention but as merely providing an illustration of the presently preferred embodiments. Other embodiments including additions, subtractions, deletions, or modifications will be obvious to those skilled in the art and are within the scope of the following claims. The scope of the disclosure should be determined by the appended claims and their legal equivalents, rather than by the examples given. As a particular example of this, the reference SLO channel can be designed with traditional laser sources, but now also with superluminescent diode laser sources; the scanning systems can include polygons, or galvos, one or two dimensional confocal systems based on spot or line scanning configurations can be used. The fiduciary channel can be a traditional optical fundus camera configuration. Still other embodiments may take full advantage of adaptive optics by incorporating e.g. deformable mirrors and a wavefront measuring device, in intra- and preretinal surgery.

The invention claimed is:

1. An ophthalmoscope apparatus for delivering short pulsed laser applications to the retina of an eye comprising:
    A. an imaging channel including a first light source, a projecting means, focusing means, and at least one detection means for producing a fiduciary reference image of said retina of said eye;
    B. a therapeutic laser channel including a femtosecond domain pulsed laser beam second light source capable of retinal photodisruption, and a second focusing means to adjust the position in depth of the waist of said beam inside said retina of said eye, further including a deflecting means for causing a fast succession of small angle deviations of said beam;
    C. a coupling means including a beam splitter to combine said imaging channel and said therapeutic laser channel, and further including a positioning means for causing a slow succession of large angle deviations of said beam, to adjust the lateral position of the waist of said beam inside said retina of said eye;
    D. a synchronizing means for establishing an appropriate duty-cycle for said pulsed laser beam to deliver a predetermined pattern of photodisruptive applications in said retina at a desired depth.

2. The ophthalmoscope apparatus of claim 1 wherein said first and said second focusing means are same.

3. The ophthalmoscope apparatus of claim 1 wherein said detection means is from the group of confocal, coherent or mixed design.

4. The ophthalmoscope apparatus of claim 1 further including the improvement of a biometric reference channel including:

A. a third light source, said coupling means aligning said third light source with said first and said second light source;

B. a coherent detection means for obtaining reference optical path length distance measurements inside said eye.

5. An ophthalmoscope apparatus for delivering femtosecond domain short pulsed laser applications to the retina of an eye comprising:

A. an imaging channel including a first light source, a first focusing means for said first light source, a single scanning means of predetermined sufficiently high bandwidth, and a detection means for collecting the returned light from said retina to provide a reference image of said retina of said eye;

B. a femtosecond domain pulsed laser beam second light source, capable of retinal photodisruption, said single scanning means also used for positioning laterally said beam of second light source onto said retina, and a second focusing means for positioning in said retina the waist of said pulsed laser beam;

C. a modulating means for adjusting the intensity of said pulsed laser beam during scanning at said sufficiently high bandwidth;

D. thereby providing an appropriate duty-cycle for said pulsed laser beam to deliver a pattern of photodisruptive applications in said retina at a predetermined depth location without the need for a moving means other than said single scanning means.

6. The ophthalmoscope apparatus of claim 5 wherein said first and said second focusing means are same.

7. The ophthalmoscope apparatus of claim 5 wherein said detection means is from the group of confocal, coherent or mixed design.

8. The ophthalmoscope apparatus of claim 5 further including the improvement of a biometric reference channel including:

A. a third light source, said coupling means aligning said third light source with said first and said second light source;

B. a coherent detection means for obtaining reference optical path length distance measurements inside said eye.

* * * * *